(12) United States Patent
Tretjak et al.

(10) Patent No.: US 12,116,339 B2
(45) Date of Patent: Oct. 15, 2024

(54) METHOD FOR PURIFYING (METH)ACRYLIC ACID

(71) Applicant: Arkema France, Colombes (FR)

(72) Inventors: Serge Tretjak, Saint Avold (FR); Aurelien Huve, Saint Avold (FR)

(73) Assignee: Arkema France, Colombes (FR)

( * ) Notice: Subject to any disclaimer, the term of this patent is extended or adjusted under 35 U.S.C. 154(b) by 195 days.

(21) Appl. No.: 17/914,387

(22) PCT Filed: Mar. 23, 2021

(86) PCT No.: PCT/FR2021/050490
§ 371 (c)(1),
(2) Date: Sep. 26, 2022

(87) PCT Pub. No.: WO2021/205090
PCT Pub. Date: Oct. 14, 2021

(65) Prior Publication Data
US 2023/0109749 A1    Apr. 13, 2023

(30) Foreign Application Priority Data
Apr. 6, 2020  (FR) .................................... 2003402

(51) Int. Cl.
| | |
|---|---|
| *C07C 51/44* | (2006.01) |
| *B01D 3/14* | (2006.01) |
| *B01D 3/34* | (2006.01) |
| *B01D 3/42* | (2006.01) |
| *C07C 51/46* | (2006.01) |
| *C07C 57/04* | (2006.01) |

(52) U.S. Cl.
CPC .............. *C07C 51/44* (2013.01); *B01D 3/143* (2013.01); *B01D 3/34* (2013.01); *B01D 3/4205* (2013.01); *C07C 51/46* (2013.01); *C07C 57/04* (2013.01)

(58) Field of Classification Search
CPC ......... C07C 51/44; C07C 57/04; B01D 3/143; B01D 3/34; B01D 3/4205
See application file for complete search history.

(56) References Cited

U.S. PATENT DOCUMENTS

| | | |
|---|---|---|
| 3,725,208 A | 4/1973 | Maezawa et al. |
| 5,504,247 A | 4/1996 | Saxer et al. |
| 7,393,976 B2 | 7/2008 | Benderly et al. |
| 8,242,308 B2 | 8/2012 | Ho et al. |
| 8,530,700 B2 | 9/2013 | Ho et al. |
| 9,371,261 B2 | 6/2016 | Fauconet |
| 10,112,885 B2 | 10/2018 | Decourcy |
| 10,815,182 B2 | 10/2020 | Fauconet et al. |
| 10,961,179 B2 | 3/2021 | Fauconet et al. |
| 2017/0174604 A1 | 6/2017 | Decourcy |
| 2018/0079706 A1 | 3/2018 | Jain et al. |
| 2019/0071382 A1* | 3/2019 | Fauconet ................ C08F 20/06 |
| 2022/0169589 A1 | 6/2022 | Tretjak et al. |

FOREIGN PATENT DOCUMENTS

WO    WO2020201661    10/2020

* cited by examiner

*Primary Examiner* — Renee Robinson
(74) *Attorney, Agent, or Firm* — Debodhonyaa Sengupta

(57) ABSTRACT

The invention relates to a process for the continuous production of acrylic acid, in the absence of organic solvent and in the absence of chemical treatment of the aldehydes, and without employing a dividing-wall column, from a gaseous reaction mixture comprising acrylic acid obtained by gas-phase oxidation of a precursor of acrylic acid.

16 Claims, 2 Drawing Sheets

[Fig. 1]
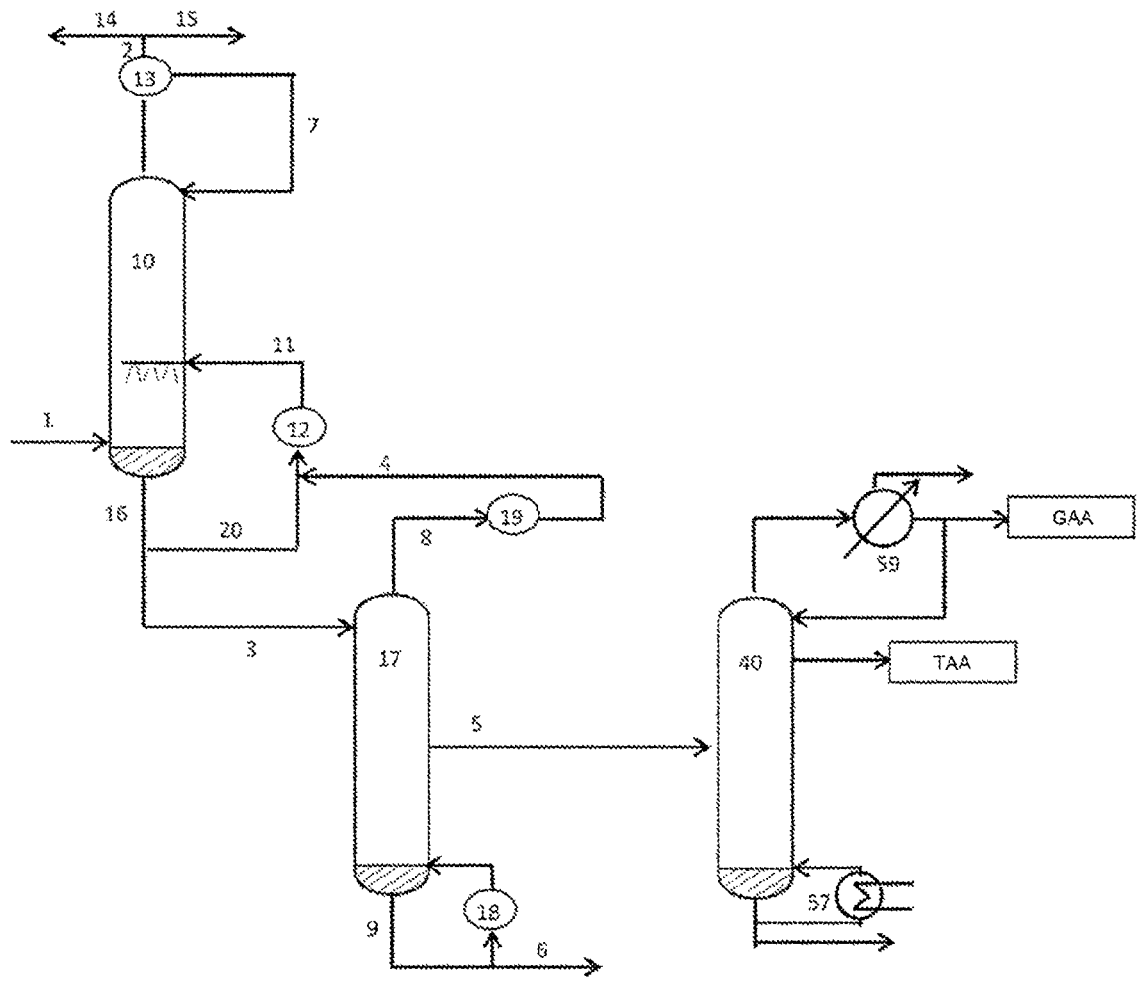

[Fig.2]
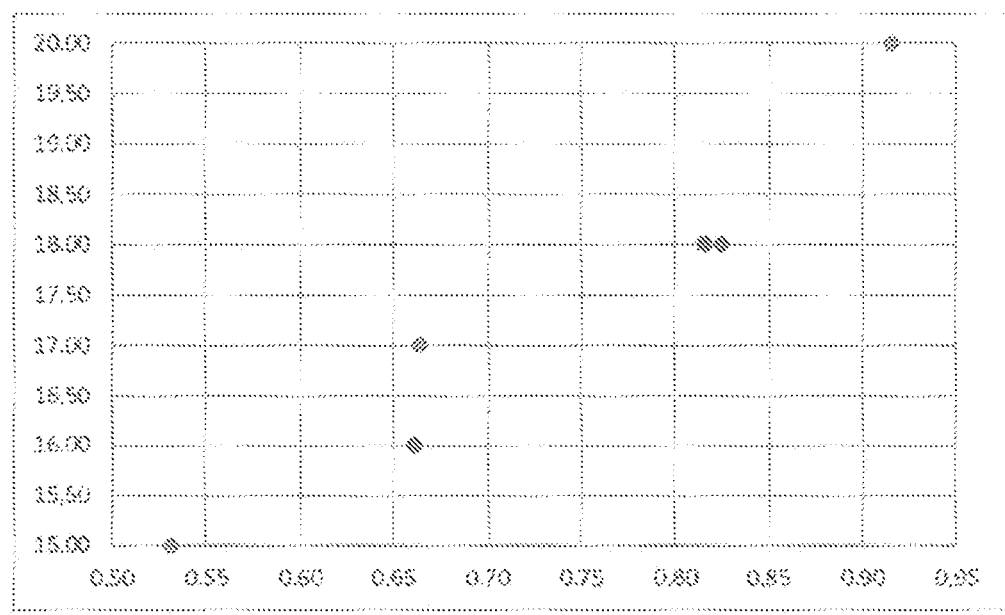

METHOD FOR PURIFYING (METH)ACRYLIC ACID

CROSS-REFERENCE TO RELATED APPLICATIONS

This application is a national stage application under 35 U.S.C. § 371 of PCT/FR2021/050490, filed Mar. 23, 2021 which claims benefit to application FR 2003402, filed Apr. 6, 2020.

FIELD OF THE INVENTION

The present invention relates to an improved process for the purification of (meth)acrylic acid, carried out in the absence of organic solvent and in the absence of a chemical treatment of the aldehydes.

TECHNICAL BACKGROUND

The process for the synthesis of acrylic acid made use of on a large industrial scale employs a reaction for the catalytic oxidation of propylene in the presence of oxygen. This reaction is generally carried out in the gas phase, and most often in two stages: the first stage carries out the substantially quantitative oxidation of the propylene to give an acrolein-rich mixture and then the second stage carries out the selective oxidation of the acrolein to give acrylic acid.

The gas mixture resulting from the second stage consists, apart from the acrylic acid, of unconverted compounds resulting from the reactants involved or of impurities generated during one at least of the two reaction stages, namely:
- of light compounds which are noncondensable under the temperature and pressure conditions normally employed, i.e. essentially: propylene, propane, nitrogen, unconverted oxygen, carbon monoxide and dioxide formed in small amounts by final oxidation;
- of light compounds which are condensable, i.e. essentially: water, light aldehydes, such as unconverted acrolein, formaldehyde, glyoxal and acetaldehyde, formic acid, acetic acid or propenoic acid;
- of heavy compounds: furfuraldehyde, benzaldehyde, maleic acid and anhydride, benzoic acid, 2-butenoic acid, phenol or protoanemonin.

The complexity of the gas mixture obtained in this process requires a set of operations in order to recover the acrylic acid contained in this gaseous effluent and to convert it into a technical or glacial grade of acrylic acid compatible with its final use, for example the synthesis of acrylic esters or the production of polymers of acrylic acid and/or of acrylic esters.

The documents EP 2 066 613, WO 2015/126704 and WO 2008/033687, based on a "solventless" technology, describe a process for the recovery of acrylic acid without use of external water or of azeotropic solvent. This process employs two distillation columns to purify the cooled gaseous reaction mixture: a) a dehydration column, b) a finishing column fed with a portion of the bottom stream from the dehydration column. During the purification/finishing stage, a stream of purified acrylic acid is recovered in the liquid or vapor form, by side stream withdrawal from the finishing column. The technical acrylic acid obtained generally has a purity of greater than 98.5%, indeed even of greater than 99.5% (contents by weight). It contains less than 0.3% of water, less than 0.075% of acetic acid and above all heavy compounds, such as aldehydes and protoanemonin.

This technical acrylic acid can be used, without further purification, to produce esters. However, this "technical" quality will not be sufficient when this acrylic acid is intended for the manufacture of polymers. In this case, it will be necessary to use "glacial" acrylic acid. This is because it is particularly important to remove certain impurities from technical AA down to extremely low levels. They are in particular certain aldehydes, such as furfuraldehyde (or furfural), benzaldehyde or acrolein, or other impurities, such as protoanemonin, compounds generated during the synthesis of acrylic acid, or also non-phenolic polymerization inhibitors, such as the phenothiazine introduced during the synthesis of acrylic acid. These compounds have a major effect on the reactivity of glacial AA when it is used in a polymerization reaction targeted at producing a high molecular weight polymer, by slowing down or inhibiting this reaction.

Glacial acrylic acid is intended subsequently for carrying out processes for the polymerization either of acrylic acid or of its ester or amide derivatives, which processes are carried out in different forms, in bulk, in solution, in suspension or in emulsion. These polymers are used as such or as copolymers in fields as varied as hygiene (for example in the production of superabsorbents), detergents, paints, varnishes, adhesives, paper, textiles or leather.

In order to obtain glacial acrylic acid from technical acrylic acid, the documents EP 2 066 613 and WO 2008/033687 indicate that the latter can be subjected to an additional treatment by fractional crystallization, as described in the U.S. Pat. No. 5,504,247 of Sulzer or in the document WO 2011/010035 of the applicant company, for the production of polymer-grade acrylic acid of renewable origin.

Furthermore, a process for the manufacture of glacial AA by distillation can be advantageous by virtue of its possibilities of energy integration when it is possible to recover the heat present in the excess energy provided by the exothermic reaction stage (in the vapor form), which cannot be carried out simply when the purification is carried out by crystallization (the latter requiring cold, and thus consumption of electricity). It is thus possible to obtain glacial acrylic acid by a distillation operation combined with a chemical treatment making it possible to remove the aldehydes. It is possible, among the reactants which can be used, to employ amines and more particularly the compounds of the family of the hydrazines, as described in the U.S. Pat. Nos. 3,725,208 and 7,393,976.

In the document WO 2017/060583, the stage of treatment of the aldehydes using a chemical agent is carried out in a purification section comprising a dehydration column, and a finishing column, preferably inside said purification section, or alternatively in a section for additional purification by distillation with one or two distillation columns, and making it possible to result in a glacial acrylic acid quality.

The document WO 2018/185423 describes the use of a dividing-wall column as a purification/finishing column in a process for the recovery of acrylic acid using two distillation columns in the absence of external organic solvent. The particular configuration of the dividing-wall column, that is to say when the dividing wall is contiguous with the upper dome of the column in the top part and not contiguous with the bottom of the column in the bottom part, makes it possible to improve the energy balance of the process while improving the technical quality of the acrylic acid recovered.

The technical acrylic acid extracted at the top of the dividing-wall column can be subjected to an additional treatment by fractional crystallization, or by distillation, optionally in the presence of a compound which reacts with the residual aldehydes. Under certain specific operating conditions, the quality of the acrylic acid obtained is that of a glacial acrylic acid.

The use of a dividing-wall distillation column remains complex and the purification described in this document cannot be adapted, without significant modification, to conventional processes for the recovery of acrylic acid using an external organic solvent.

The document WO 2016/142608 describes a process for the recovery of (meth)acrylic acid without use of azeotropic solvent, from a gaseous reaction mixture comprising (meth) acrylic acid obtained by gas-phase oxidation of a precursor of the (meth)acrylic acid, comprising at least the following stages:
  i) the gaseous reaction mixture is subjected to a dehydration without using azeotropic solvent in a first column, called dehydration column, resulting in a top stream, a portion at least of which is condensed and returned to the dehydration column in reflux form, and in a bottom stream;
  ii) the dehydration column bottom stream is subjected, at least in part, to a distillation at a pressure below atmospheric pressure in a second column, called finishing column, resulting in a top stream and in a bottom stream containing heavy compounds;
  iii) a stream of (meth)acrylic acid is recovered by side stream withdrawal from the finishing column and/or at the bottom of the finishing column;
  said process being characterized in that the top stream from the finishing column is at least partially subjected to a dry vacuum pump condensation system, forming a condensate, which is returned to the dehydration column, and a final gaseous effluent.

This document indicates that a stream of (meth)acrylic acid 16 is recovered by side stream withdrawal from the finishing column (stage iii), at a side level preferably located below the feed point of said column, and that said stream 16 can also be subjected to a purification by distillation, optionally coupled with a crystallization treatment.

The applicant company has described, in its application FR 1 903 519, a process for the purification of a technical acrylic acid in the absence of a chemical reactant for the treatment of aldehydes, producing a stream of glacial acrylic acid which is withdrawn via a side outlet of the distillation unit, a stream essentially comprising light compounds being extracted at the top of the distillation unit, and a stream of acrylic acid comprising heavy compounds being recovered at the bottom of the distillation unit.

There now exists the need to provide an optimized purification process "without solvent" and "without chemical treatment agent" which makes it possible to obtain glacial acrylic acid and technical acrylic acid at the same time, while optimizing the overall energy consumption of the entire separation line as well as those of the plants using these technical or glacial acrylic acids. By adapting the glacial acrylic acid/technical acrylic acid production ratio, the process according to the invention makes it possible to match market demands.

SUMMARY OF THE INVENTION

A subject matter of the present invention is a process for the continuous production of acrylic acid, in the absence of organic solvent and in the absence of chemical treatment of the aldehydes, and without employing a dividing-wall column, from a gaseous reaction mixture comprising acrylic acid obtained by gas-phase oxidation of a precursor of acrylic acid, said process employing three distillation columns and comprising the following stages:
  a) said gaseous reaction mixture is subjected to a dehydration without using an azeotropic solvent, in a first distillation column called a dehydration column, resulting in a top stream, a portion at least of which is condensed and returned to the dehydration column in the reflux form, and in a bottom stream, a portion at least of which is returned as reflux in the lower part of the dehydration column to form a recirculation loop;
  b) the bottom stream from the dehydration column is sent, at least in part, to a second distillation column called a finishing column. The finishing column is fed on the top first third of the column and the light products are distilled, the heavy products are removed at the bottom of this column, technical grade acrylic acid is obtained by gaseous-phase side stream withdrawal placed in the lower first third of this column. The light products composed partly of water and of acetic acid are extracted at the top of the feed section, then recycled, after condensation, at least partly in the recirculation loop at the bottom of the dehydration column or as liquid reflux at the top of this column called finishing column;
  c) the technical acrylic acid extracted by the gas-phase side stream withdrawal feeds a third distillation column which makes it possible to obtain technical acrylic acid by side stream withdrawal in the lower third of this column, and glacial acrylic acid at the top of this column; a portion at least of the latter is condensed and returned to this column in reflux form. In addition, the residual product resulting from the distillation of the glacial acrylic acid, recovered at the bottom of the distillation unit, can be advantageously recycled to an esterification plant manufacturing $C_1$-$C_8$ acrylic esters without additional purification, which would be essential in the event of use of an agent for the chemical treatment of the aldehydes.

The invention is targeted at continuously producing technical acrylic acid as well as glacial acid with an optimized purification cost. It is based on the implementation under specific conditions of a purification process involving a reduced number of distillation columns and not requiring an external organic solvent, nor a chemical treatment intended to reduce the content of aldehydes, nor the use of a dividing-wall distillation column.

The process according to the invention makes it possible to simultaneously produce, on conclusion of the last distillation stage:
  a stream of glacial acrylic acid having a purity of greater than 99.7% and contents by weight of impurities as follows: furfural content <2 ppm; content of total aldehydes (furfural, benzaldehyde, acrolein)<10 ppm, preferably <4 ppm; protoanemonin content <2 ppm, and
  a stream of technical acrylic acid having a purity of greater than 99.5% by weight and containing less than 0.3% of water, less than 0.075% of acetic acid, furfural content >50 ppm and <0.05%, benzaldehyde content >50 ppm and <0.05%, protoanemonin content >50 ppm and <0.05%.

FIGURES

FIG. 1 diagrammatically represents an embodiment of an installation according to the invention.

FIG. 2 is a diagram representing the number of theoretical stages at total reflux as a function of the hydraulic traffic in a column for distilling a binary acetic acid/propenoic acid mixture.

DETAILED DESCRIPTION

The invention is now described in more detail and in a nonlimiting fashion in the description which follows.

In the present invention, the term "(meth)acrylic" means "acrylic" or "methacrylic". For the sake of simplicity, the continuation of the disclosure will refer to the production of acrylic acid but also applies by analogy to the production of methacrylic acid.

The term "external organic solvent" denotes any organic compound in which (meth)acrylic acid is soluble and the origin of which is external to the process, used as absorption, extraction or azeotropic distillation solvent.

The term "azeotropic solvent" denotes any organic solvent exhibiting the property of forming an azeotropic mixture with water.

The term "noncondensable" denotes the compounds, the boiling point of which is lower than the temperature of 20° C. under atmospheric pressure.

The term "light" describing the byproduct compounds denotes the compounds, the boiling point of which is below that of (meth)acrylic acid under the working pressure under consideration and, by analogy, the term "heavy" denotes the compounds, the boiling point of which is above that of (meth)acrylic acid.

All the percentages and contents indicated are by weight.

The term "technical acrylic acid" corresponds to a solution of acrylic acid with a purity of greater than 98.5% and containing less than 0.3% of water, less than 0.075% of acetic acid, furfural content >50 ppm and <0.05%, benzaldehyde content >50 ppm and <0.05%, protoanemonin content >50 ppm and <0.05%. The term "technical" indicates here that the (meth)acrylic acid meets very high quality criteria making possible its use in the manufacture of ester without further purification treatment. The process according to the invention makes it possible to guarantee a quality of technical acrylic acid which is always close to 99.5%, which makes it possible to reduce the amount of technical acrylic acid to be employed in ester manufacturing processes. By way of example, for an installation producing 100 000 T/year of 2-ethylhexyl acrylate, the amount by weight of 100% pure acrylic acid is 39 000 T/year. Increasing the quality of the technical acrylic acid from 98.5% to 99.5% makes it possible to use 400 T less of technical acrylic acid in the process and thus to reduce the amount of byproducts to be treated by 400 T.

This technical acrylic acid can be used, without further purification, to produce esters. However, this "technical" quality will not be sufficient when this acrylic acid is intended for the manufacture of polymers. In this case, it will be necessary to use "glacial acrylic acid", which is defined as follows: having a purity of greater than 99.7% and contents of impurities as follows: furfural content <2 ppm; content of total aldehydes (furfural, benzaldehyde, acrolein) <10 ppm, preferably <4 ppm; protoanemonin content <2 ppm.

The present invention relates to a process for the purification of (meth)acrylic acid in the absence of organic solvent and in the absence of a chemical treatment of the aldehydes, from a gaseous reaction mixture comprising (meth)acrylic acid obtained by gas-phase oxidation of a precursor of (meth)acrylic acid, said process comprising the following stages:
 a) subjecting said reaction mixture to a dehydration, without using azeotropic solvent, in a dehydration column, resulting in a top stream and a bottom stream being obtained,
 b) sending at least a portion of said bottom stream from the dehydration column into the upper part of a finishing column, where the light products are distilled, the heavy products are removed at the bottom of this column and a side stream comprising liquid-phase technical acrylic acid is withdrawn,
 c) sending said side stream from the finishing column to the lower third of a third distillation column, resulting in a top stream, a side stream and a bottom stream being obtained, said top stream charged with glacial acrylic acid being subjected to a condensation and then returned after condensation, partly in this column in reflux form and partly being recovered, said side stream charged with technical acrylic acid being withdrawn in the half of the lower part of said distillation column.

According to one embodiment, at least a portion of the top stream from the dehydration column is subjected to a condensation, then is returned to the dehydration column in reflux form.

According to one embodiment, at least a portion of the bottom stream from the dehydration column is returned in reflux form to the lower part of this column to form a recirculation loop.

According to one embodiment, said light products, composed of water and of acetic acid, are extracted at the top of the finishing column, then subjected to a condensation. At least a portion of the condensate thus obtained is returned to the dehydration column to be mixed with the stream of said recirculation loop. According to one embodiment, at least a portion of said condensate is recycled as liquid reflux at the top of the finishing column.

According to one embodiment, the residual stream recovered at the bottom of the distillation column is recycled to an esterification plant manufacturing $C_1$-$C_8$ (meth)acrylic esters, without additional purification.

According to one embodiment, the side stream withdrawn from the finishing column comprises a solution containing at least 98.5% of acrylic acid, less than 0.3% of water, less than 0.075% of acetic acid, and having a furfural content of greater than 50 ppm and less than 0.05%, a benzaldehyde content of greater than 50 ppm and less than 0.05%, and a protoanemonin content of greater than 50 ppm and less than 0.05%.

According to one embodiment, said top stream from the distillation column comprises, after condensation, a solution containing at least 99.7% of acrylic acid and contents of impurities as follows: furfural content of less than 2 ppm, a content of total aldehydes (furfural, benzaldehyde, acrolein) of less than 10 ppm, preferably than 4 ppm, and a protoanemonin content of less than 2 ppm.

According to one embodiment, the gaseous reaction mixture to be purified comprises a water/acrylic acid ratio by weight of between 0.3 and 2, preferably between 0.3 and 1.2. This reaction mixture comprises, in addition to water and acrylic acid, noncondensable light products such as nitrogen, oxygen, carbon monoxide and carbon dioxide, as well as various light or heavy byproducts of different chemical natures which can be light aldehydes, such as acrolein, formaldehyde, acetaldehyde or glyoxal, heavy aldehydes, such as furfuraldehyde or benzaldehyde, light acids, such as formic acid, acetic acid or propionic acid, heavy acids, such as maleic acid, benzoic acid or 2-butenoic acid, and protoanemonin, a heavy compound of lactone type.

According to one embodiment, the bottom stream from the dehydration column essentially comprises acrylic acid (84-90%), acetic acid (2-10%), water (2-10%) and heavy byproducts.

According to one embodiment, the dehydration column comprises from 5 to 50 theoretical plates, preferably from 20 to 30 theoretical plates.

Advantageously, the dehydration column operates at atmospheric pressure or slightly higher, up to an absolute pressure of $1.5 \times 10^5$ Pa.

Advantageously, the temperature in the upper part of the dehydration column is at least 40° C., preferably is between 40° C. and 80° C. The temperature of the bottom stream from the dehydration column preferably does not exceed 120° C.

According to one embodiment, the finishing column is a conventional distillation column comprising from 5 to 30 theoretical plates, preferably from 8 to 20 theoretical plates. The finishing column operates at a pressure below atmospheric pressure, making it possible to operate at relatively low temperatures, thus preventing the polymerization of the unsaturated products present and minimizing the formation of heavy byproducts.

Advantageously, the finishing column operates under an absolute pressure ranging from 5 kPa to approximately 60 kPa, the temperature of the top stream advantageously being between 40° C. and approximately 90° C. and the temperature of the bottom stream being between 60° C. and 120° C.

According to one embodiment, the distillation column is a conventional distillation column comprising from 15 to 30 theoretical plates, preferably from 20 to 25 theoretical plates. This column operates at a pressure below atmospheric pressure, making it possible to operate at relatively low temperatures, thus preventing the polymerization of the unsaturated products present and minimizing the formation of heavy byproducts.

According to one embodiment, polymerization inhibitors, preferentially hydroquinone methyl ether (HQME), manganese acetate, hydroquinone, phenothiazine, or their mixtures, in appropriate amounts, are injected at the top of all the columns to protect the condensed stream against polymerization at the condenser, in the storage tank and during transportation before use of the acrylic acid, thus meeting the requirements of reactivity in polymerization.

According to one embodiment, at least one inhibitor is also injected upstream of each condenser, so as to prevent the formation of polymer during the condensation of the distilled gaseous mixture and in the column, by virtue of the presence of this inhibitor in the liquid reflux returned at the column top.

According to one embodiment, air or depleted air is injected at the lower part of the finishing and distillation columns, preferably in a proportion by volume of 0.1% to 0.5% of oxygen with respect to the total flow rate of distilled AA.

The sections of the distillation column are equipped with counterflow plates characterized by the absence of overflows or weirs, such as: plates of the type of Dual Flow, Turbo Grid, Ripple Trays or wireless valve trays. These counterflow plates operate in the way described by J P. Wauquier, Institut Français du Pétrole [French Petroleum Institute], *Le Raffinage du Pétrole* [*Oil Refining*], 1998, Volume 2: Procédés de séparation [Separation Processes], Chapter 5, p 287. Liquid and gas pass alternately through the orifices, which creates the self-cleaning nature. These plates can be effective in carrying out a separation when it operates in their design condition, with, however, a severely limited operating flexibility because:

at low gas flow rate, the liquid tends to pass through the orifices quickly without staying on the surface of the plate, thus reducing the contact time between the phases and consequently the efficiency of the plates;

at high gas flow rate, the liquid on the plate is thrown up, can no longer flow through the orifices resulting in a clogging phenomenon.

The paper by J. A. Garcia and J. R. Fair in *Ind. Eng. Res.*, 2002, 41, 632-1640, or the appended FIG. 2 clearly illustrate the loss in efficiency of the column as a function of the hydraulics of the column and thereby of the load of the column. Thus, when the gas flow rate is reduced by 2, the efficiency of a plate can decrease from 80% to 40% (see FIG. 3 of this publication).

It is well understood that, with such a variation in separation efficiency, the design of an installation making it possible to obtain variable proportions of technical acrylic acid and of glacial acrylic acid proves to be problematic and the present invention is intended to provide a solution to this problem.

Advantageously, the distillation column operates under an absolute pressure ranging from 5 kPa to approximately 60 kPa, the temperature of the top stream advantageously being between 40° C. and approximately 90° C. and the temperature of the bottom stream being between 60° C. and 120° C.

For the distillation column, the reflux ratio, which can be defined as the flow rate of recycling from the column top to the column, with respect to that of side stream withdrawal, is between 1.5 and 4, preferably between 2 and 3, for example is equal to 2.5. Under these conditions, it is possible to obtain a good compromise between the column size and the number of separation stages to be used and the energy to be employed to ensure this separation.

According to the embodiment of the process represented in FIG. 1, a gaseous reaction mixture 1 comprising acrylic acid obtained by gas-phase oxidation of a precursor of acrylic acid feeds a first distillation column 10. The gaseous reaction mixture can be cooled beforehand before being subjected to a dehydration in the dehydration column 10.

The dehydration column results in a top stream 2, at least a portion of which is condensed in a condenser 13 and returned to the dehydration column in reflux form 7 to absorb the acrylic acid, the other portion (streams 14 and 15) comprising the noncondensable light compounds being generally sent partially or completely to a purification device or recycled in part to other stages of the process for the production of acrylic acid, preferably in a stage located upstream of the reactor for the production of the reaction mixture 1.

The entire top stream from the dehydration column can be sent to the top condenser 13.

The aim of the dehydration stage is to remove, in a top stream, the bulk of the water present in the reaction mixture but also the noncondensable light compounds and the condensable light compounds. It generates a top stream 2 comprising the bulk of the water and of the light compounds, with acrylic acid and heavy compounds in a very small amount, and a bottom stream 16 depleted in light compounds comprising virtually all of the acrylic acid with heavy byproducts, and a content by weight of water generally of less than 10%, preferably of less than 7%.

The bottom stream 16 from the dehydration column is sent, at least in part (stream 3), to the top of a second distillation column 17, called finishing column, in which a top stream 8 and a bottom stream 9 are separated.

A portion 20 of the bottom liquid stream 16 from the dehydration column is sent to a heat exchanger 12, which can be a heater or a cooler, and reinjected into the dehydration column, so as to constitute a bottom recirculation loop. Preferably, the part 11 from the bottom loop is reinjected between the feed of the gaseous reaction mixture and the dehydration column top.

The remainder (stream 3) of the liquid stream 16 is sent as feed of the finishing column 17. This distillation column is combined, at the bottom, with at least one reboiler 18 and, at the top, with a condenser 19.

The top gas stream 8 from the finishing column is sent to the condenser 19, and the exiting liquid stream 4 is returned to the dehydration column, mixed with the stream from the bottom loop of the dehydration column. The top stream 8 essentially comprises water and condensable light byproducts.

The stream 9 separated at the bottom of the finishing column comprises the bulk of the heavy byproducts, in particular of the Michael addition products, such as 3-acryloyloxypropionic acid, maleic anhydride/acid, benzoic acid, the acrylic acid dimer and also polymerization inhibitors. This stream 9 can be partly recycled in the lower part of the finishing column or used as starting material for the acrylic esters after removal of the acrylic acid dimers.

A stream 5 comprising purified acrylic acid in liquid or vapor form is extracted from the finishing column by side stream withdrawal. This stream 5 corresponds to technical acrylic acid.

This stream 5 after condensation is sent to a third distillation column in order to obtain glacial acrylic acid and technical acrylic acid. In this configuration, all of the technical acrylic acid resulting from the finishing column feeds the column for obtaining glacial acrylic acid, thus ensuring a constant hydraulic feed load for this third column.

This distillation unit (40) comprises, in particular after condensation, a reflux at the top of the distillation column, a withdrawal of the heavy products at the column bottom, a liquid withdrawal of glacial acrylic acid at the column top (gAA) and a gas phase collected towards the vent of the unit and a side stream withdrawal for the technical acrylic acid.

This distillation column is combined, at the bottom, with at least one reboiler 57 and, at the top, with a condenser 59.

The column 40 is fed in the first third of the lower part.

The glacial acrylic acid after condensation is withdrawn at the column top. Noncondensables (air, noncondensed organics) are sent to the vent network of the process. The technical acrylic acid is withdrawn at least 1 plate below the withdrawal of glacial acrylic acid, preferably in the first half of the column lower part, indeed even in the first third of the column lower part. This side stream withdrawal can be carried out in the gas or liquid phase, preferably liquid phase.

The bottom product from the column can advantageously be remixed with this technical acrylic acid while obtaining a product having a purity of greater than 99.5%.

The top gas stream from the column 40 is sent to the condenser 59, and the exiting liquid stream is glacial acrylic acid having a purity of greater than 99.7% and contents by weight of impurities as follows: furfural content <2 ppm; content of total aldehydes (furfural, benzaldehyde, acrolein) <10 ppm, preferably <4 ppm; protoanemonin content <2 ppm.

The ratio by weight of the stream withdrawn at the bottom to the feed stream is between 1% and 40%, preferably between 5% and 10%.

The stream recovered at the bottom of the distillation unit 40 is advantageously remixed with the stream of technical acrylic acid to an esterification unit without additional treatment with a purity of at least 99.5%.

At the top of the condenser 59, the residual gas stream is sent to the vent circuit of the process.

The invention will now be illustrated by the following examples, which do not have the aim of limiting the scope of the invention, defined by the appended claims.

EXAMPLES

The following examples illustrate the invention without limiting it.

In the examples, the percentages are shown by weight for the main compounds, unless otherwise indicated, and the following abbreviations were used:

$H_2O$: water
ACRA: acrylic acid
Benzal: benzaldehyde
ACA: acetic acid
FURF: furfuraldehyde
DIMR: acrylic acid dimers
Propenoic Acid
Protoanemonin was compared in our ASPEN simulations to benzaldehyde.

Example 1: Separation efficiency of a binary acetic acid/propenoic acid mixture in a distillation column with a diameter of 300 mm comprising 50 Dual Flow plates at total reflux at a head pressure of 90 mmHg.

The analysis of the top and bottom compositions by gas chromatography at different percentages of clogging makes it possible, after use of the Aspen software, to determine the number of theoretical stages at total reflux as a function of the hydraulic traffic in the column.

As shown in the graph of the appended FIG. 2, the separation efficiency, which is expressed here in terms of number of theoretical stages, is highly dependent on the hydraulics of the column.

Example 2 (FIG. 1): Purification of a gaseous reaction mixture comprising acrylic acid obtained by gas-phase oxidation of a precursor of acrylic acid, by means of three distillation columns.

The process for the recovery of technical acrylic acid and of glacial acrylic acid represented in FIG. 1 provides, as side stream withdrawal from the finishing column (17), a stream (5) of purified acrylic acid.

The bottom stream (3) from the dehydration column (10) constitutes the feed at the upper plate of the finishing column (17). The finishing column (17) comprises 17 theoretical stages, and the side stream withdrawal is carried out at the theoretical plate 16, counting from the top of the column.

The stream (5) feeds, after condensation and addition of a stabilization solution, the column (40) comprising 24 theoretical stages at the plate 20. The glacial acrylic acid is withdrawn at the column top after condensation and partial return of a portion of the stream to the column to ensure the reflux of the latter. The acrylic acid at the bottom of the column can be remixed with the technical acrylic acid obtained as side stream withdrawal. The column is also stabilized at the condenser and at reflux and air is injected at the column bottom (not represented). The technical acrylic acid in a proportion of 50% of the feed stream of the column is withdrawn at the plate 16.

The different stream qualities are presented in table 1 below.

TABLE 1

| STREAM | | 3 | 8 | 6 | Feed C40 | GAA | TAA | Bottom product C40 |
|---|---|---|---|---|---|---|---|---|
| Temperature | C. | 69.6 | 72.9 | 30.0 | 20.1 | 20.0 | 93.2 | 95.3 |
| Pressure | bar | 3.2 | 0.1 | 0.2 | 1.0 | 0.1 | 0.2 | 0.2 |
| Flow rate by weight | kg/h | 188.2 | 121.4 | 6.5 | 65.4 | 32.0 | 32.7 | 4.0 |
| Mass Fractions | | | | | | | | |
| $H_2O$ | | 5.32% | 8.25% | 0.00% | 0.01% | 0.01% | 0.00% | 0.00% |
| ACA | | 11.00% | 17.04% | 0.01% | 0.05% | 0.09% | 0.01% | 0.00% |
| ACRA | | 82.97% | 73.84% | 82.73% | 99.76% | 99.85% | 99.86% | 97.58% |
| FURF | | 0.01% | 0.01% | 0.06% | 0.02% | 0.000088% | 0.028129% | 0.16% |
| BENZALD | | 0.02% | 0.01% | 0.15% | 0.03% | 0.000000% | 0.021777% | 0.34% |
| DIMR | | 0.24% | 0.00% | 6.80% | 0.00% | 0.000000% | 0.001142% | 0.05% |

With this process, technical acrylic acid of very high quality is obtained, which makes it possible to also upgrade the bottom product from C40 by mixing. In this case, the purity is 99.57%.

With less than 1 ppm of furfural and no more benzaldehyde, the glacial acrylic acid meets the specifications.

The energy employed for the finishing column and for obtaining the glacial acrylic acid is 40 043 kcal/h.

The invention claimed is:

1. A process for the purification of (meth)acrylic acid in an absence of organic solvent and in an absence of a chemical treatment of aldehydes, from a gaseous reaction mixture comprising (meth)acrylic acid obtained by gas-phase oxidation of a precursor of (meth)acrylic acid, said process comprising the following stages:
    subjecting said reaction mixture to a dehydration, without using azeotropic solvent, in a dehydration column, resulting in a top stream and a bottom stream being obtained,
    sending at least a portion of said bottom stream from the dehydration column into an upper part of a finishing column, where light products are distilled, heavy products are removed at a bottom of the finishing column and a side stream is withdrawn,
    sending said side stream from the finishing column to a lower third of a third distillation column, resulting in a top stream, a side stream and a bottom stream being obtained, said top stream being subjected to a condensation and then returned after condensation, partly in the third distillation column in reflux form and partly being recovered, said side stream being withdrawn in a half of a lower part of said third distillation column.

2. The process as claimed in claim 1, in which at least a portion of the top stream from the dehydration column is subjected to condensation, then is returned to the dehydration column in reflux form.

3. The process as claimed in claim 1 in which a portion of the bottom stream from the dehydration column is returned in reflux form to a lower part of the dehydration column to form a recirculation loop.

4. The process as claimed in claim 3 in which said light products, composed of water and acetic acid, extracted at a top of the finishing column, are subjected to a condensation forming a condensate, at least a portion of the condensate thus obtained being returned to the dehydration column to be mixed with a stream of said recirculation loop.

5. The process as claimed in claim 1 in which a residual stream recovered at a bottom of the third distillation column is recycled to an esterification plant manufacturing $C_1$-$C_8$ (meth)acrylic esters, without additional purification.

6. The process as claimed in claim 1 in which the side stream withdrawn from the finishing column comprises a solution containing at least 98.5% of acrylic acid, less than 0.3% of water, less than 0.075% of acetic acid, and having a furfural content of greater than 50 ppm and less than 0.05%, a benzaldehyde content of greater than 50 ppm and less than 0.05%, and a protoanemonin content of greater than 50 ppm and less than 0.05%.

7. The process as claimed in claim 1 in which the top stream from the third distillation column comprises, after condensation, a solution containing at least 99.7% of acrylic acid and contents of impurities as follows: furfural content of less than 2 ppm, a content of total aldehydes (furfural, benzaldehyde, acrolein) of less than 10 ppm, and a protoanemonin content of less than 2 ppm.

8. The process as claimed in claim 1 in which the side stream withdrawal stream from the third distillation column comprises, after condensation, a solution containing at least 99.7% of acrylic acid, less than 0.3% of water, a furfural content of greater than 50 ppm, a benzaldehyde content of greater than 50 ppm and a protoanemonin content of greater than 50 ppm.

9. The process as claimed in claim 1 in which the bottom stream from the third distillation column containing at least 97% of acrylic acid is mixed with an acrylic acid stream obtained in side stream withdrawal from the third distillation column or recycled to an esterification unit without additional treatment.

10. The process as claimed in claim 1 in which the dehydration column comprises from 5 to 50 theoretical plates and operates at atmospheric pressure or higher, up to an absolute pressure of $1.5 \times 10^5$ Pa.

11. The process as claimed in claim 1 in which the temperature in the upper part of the dehydration column is at least 40° C. and the temperature of the bottom stream from the dehydration column is less than 120° C.

12. The process as claimed in claim 1 in which the finishing column comprises from 5 to 30 theoretical plates and operates under an absolute pressure ranging from 5 kPa to 60 kPa, the temperature of the top stream being between 40° C. and approximately 90° C. and the temperature of the bottom stream being between 60° C. and 120° C.

13. The process as claimed in claim 1 in which the distillation column operates under an absolute pressure ranging from 5 kPa to approximately 60 kPa, the temperature of the top stream being between 40° C. and approximately 90° C. and the temperature of the bottom stream being between 60° C. and 120° C.

14. The process as claimed in claim 1 in which the reflux ratio of the distillation column, defined as the flow rate of recycling from the top to the column, with respect to that of the withdrawal of (meth)acrylic acid at the column top, is between 1.5 and 4.

15. The process as claimed in claim 1 in which a polymerization inhibitor chosen from hydroquinone methyl ether, manganese acetate, hydroquinone, phenothiazine and mixtures thereof are injected at the top of all the columns.

16. The process as claimed in claim 1 in which the ratio for obtaining glacial acrylic acid/technical acrylic acid varies from 10% to 90%.

\* \* \* \* \*